(12) United States Patent
Kermani et al.

(10) Patent No.: US 7,794,658 B2
(45) Date of Patent: Sep. 14, 2010

(54) OPEN CIRCUIT DELAY DEVICES, SYSTEMS, AND METHODS FOR ANALYTE MEASUREMENT

(75) Inventors: Mahyar Z. Kermani, Pleasanton, CA (US); Edward Docherty, Inverness (GB); John McInulty, Inverness (GB)

(73) Assignee: LifeScan, Inc., Milpitas, CA (US)

( * ) Notice: Subject to any disclaimer, the term of this patent is extended or adjusted under 35 U.S.C. 154(b) by 540 days.

(21) Appl. No.: 11/782,865

(22) Filed: Jul. 25, 2007

(65) Prior Publication Data

US 2009/0027040 A1 Jan. 29, 2009

(51) Int. Cl.
*G01R 17/02* (2006.01)
(52) U.S. Cl. .................. 422/82.01; 422/82.02; 436/149; 436/150; 324/76.11; 324/123 R
(58) Field of Classification Search ............... 422/82.01; 436/149, 150; 324/76.11, 123
See application file for complete search history.

(56) References Cited

U.S. PATENT DOCUMENTS

| 5,266,179 | A | 11/1993 | Nankai et al. |
| 5,366,609 | A | 11/1994 | White et al. |
| 5,565,085 | A | 10/1996 | Ikeda et al. |
| 6,193,873 | B1 | 2/2001 | Ohara et al. |
| 6,645,368 | B1 | 11/2003 | Beaty et al. |
| 2003/0203498 | A1* | 10/2003 | Neel et al. ............... 422/82.01 |
| 2004/0251131 | A1 | 12/2004 | Ueno et al. |
| 2007/0084734 | A1 | 4/2007 | Roberts et al. |

FOREIGN PATENT DOCUMENTS

| EP | 1 729 119 A1 | 5/2006 |
| WO | WO 02/077633 A1 | 10/2002 |
| WO | WO 2005/119234 A2 | 12/2005 |
| WO | WO 2006/070200 A1 | 7/2006 |
| WO | WO 2006/074927 A1 | 7/2006 |

OTHER PUBLICATIONS

Texas Instruments Incorporated, OPA847 Production Data; *Wideband, Ultra-Low Noise, Voltage-Feedback Opertional Amplifier with Shutdown*, pp. 28, Jul. 2002, Revised Apr. 2006, Texas Instruments, Inc., Dallas, Texas.
Maxim, *Low-Power, 16-Bit Multichannel DAS with Internal Reference, 10-Bit DACs, and RTC data sheet*, pp. 49, Oct. 2001, Maxim Integrated Products, USA.

* cited by examiner

*Primary Examiner*—Jill Warden
*Assistant Examiner*—Sharon Pregler

(57) ABSTRACT

System, circuits, and methods to reduce or eliminate uncompensated voltage drop between an electrode of an electrochemical cell usable for analyte measurement. In one example, a system is provided that includes a test strip, a reference voltage circuit, an operational amplifier connected to the reference voltage circuit to provide a pre-determined fraction of a reference voltage substantially equal to the test voltage applied to the first line, the operational amplifier having an output configured for one of a connected or disconnected state to the first line, and a processing circuit connected to the output of the operational amplifier and the first line such that, during a disconnected state between the output and the first line, the processing circuit remains in connection with the first line. In another example, a method of measuring an electrochemical reaction of an electrochemical cell is provided that includes applying a test voltage to the first electrode and connecting the second electrode to ground; uncoupling the first electrode from the output of the circuit while allowing electrical communication from the first electrode to the processor; and coupling the first electrode to the output to measure a test current generated in the electrochemical cell without an uncompensated voltage drop.

12 Claims, 3 Drawing Sheets

OPEN CIRCUIT DELAY DEVICES, SYSTEMS, AND METHODS FOR ANALYTE MEASUREMENT

BACKGROUND

A test meter may use a test strip for measuring an analyte in a physiological fluid such as blood. For example, an electrochemical test meter and an electrochemical test strip may be used for a blood glucose measurement by people with diabetes. During the blood glucose measurement, the test meter may use a poise delay or open circuit for a pre-determined time period. During the poise delay or open circuit, the test meter does not apply a test current or test voltage to the test strip. One or more switches may be connected to one of the test strip contacts of the test meter for creating the open circuit, as shown and described in U.S. Pat. No. 5,565,085.

SUMMARY

By utilization of various technical features described exemplarily herein, various devices, systems, and methodologies have been achieved to improve measurement accuracy. These technical features are believed to be heretofore unrecognized and unavailable in the conventional system. In particular, in one embodiment, a system to determine analyte concentration in a sample is provided. The system includes a test strip connector, reference voltage circuit, operational amplifier, and a processor. The connector has a first line configured to connect to a first electrode of a test strip and a second line configured to connect to a second electrode of the test strip. The reference voltage circuit provides an output voltage and the operational amplifier is connected to the reference voltage circuit to provide a pre-determined fraction of a reference voltage substantially equal to the test voltage applied to the first line. The operational amplifier has an output configured for one of a connected or disconnected state to the first line. The processing circuit is connected to the output of the operational amplifier and the first line such that, during a disconnected state between the output and the first line, the processing circuit remains in connection with the first line.

In yet another embodiment, a circuit for analyte measurement is provided. The circuit includes a test strip connector, operational amplifier, and a switch. The test strip connector has a first line configured to connect to a first electrode of a test strip and a second line configured to connect a second electrode of the test strip to a ground. The operational amplifier has a first input connected to a reference voltage circuit and a second input connected to both the first line and to an output of the operational amplifier via a feedback resistor. The switch is disposed between the output and the second input of the operational amplifier to connect the output to the first line in a closed state of the switch and to disconnect the output from the first line in an opened state of the switch.

In an alternative embodiment, a circuit for analyte measurement is provided. The circuit includes a test strip connector and an operational amplifier. The test strip connector has a first line configured to connect to a first electrode of a test strip and a second line configured to connect a second electrode of the test strip to a ground. The operational amplifier has a first input connected to a reference voltage circuit and a second input connected to both the first line and to an output of the operational amplifier via a feedback resistor. The operational amplifier further includes a shut down circuit configured to place the operational amplifier in a shut down mode.

In yet another embodiment, a method of measuring an electrochemical reaction of an electrochemical cell is provided with a circuit. The electrochemical cell includes first and second electrodes. The circuit has a first input connected to a voltage source, a second input connected to the first electrode and a feedback coupled to an output of the circuit, which output of the circuit is connected to a processor. The method can be achieved by: applying a test voltage to the first electrode and connecting the second electrode to ground; uncoupling the first electrode from the output of the circuit while allowing electrical communication from the first electrode to the processor; and coupling the first electrode to the output to measure a test current generated in the electrochemical cell without an uncompensated voltage drop.

These and other embodiments, features and advantages will become apparent to those skilled in the art when taken with reference to the following more detailed description of the invention in conjunction with the accompanying drawings that are first briefly described.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements), of which.

DETAILED DESCRIPTION OF ILLUSTRATIVE EMBODIMENTS

The following detailed description should be read with reference to the drawings, in which like elements in different drawings are identically numbered. The drawings, which are not necessarily to scale, depict selected exemplary embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. In addition, as used herein, the terms "patient", "host" and "subject" refer to any human or animal subject and are not intended to limit the systems or methods to human use, although use of the subject invention in a human patient represents a preferred embodiment.

Figure 1:
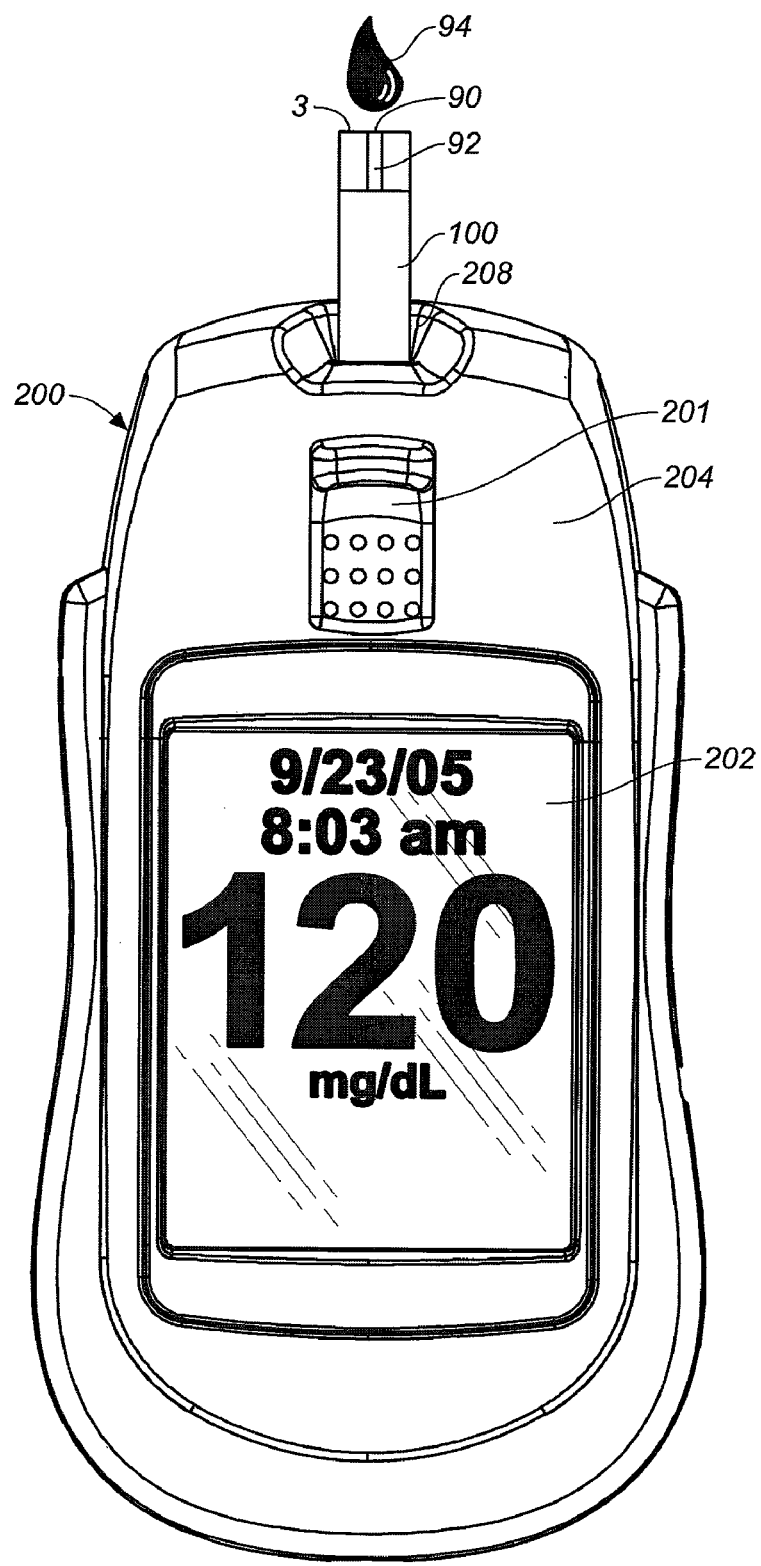
FIG. 1 is a simplified front view of a test strip that is inserted into a test meter.

FIG. 1 is a simplified plan view of a test strip 100 inserted into a test meter 200. An example of a test meter and a test strip may be the commercially available OneTouch® Ultra® glucose meter and the OneTouch® Ultra® glucose test strip (Milpitas, Calif. 95035). A description of a test strip and a test meter that may be suitable for use as an illustrative embodiment in accord with the present invention may be found in International Publication No. WO/2004040285 A2 and filed U.S. patent application Ser. No. 11/252,296 (filed on Oct. 17, 2005), which are hereby fully incorporated by reference herein.

Test meter 200 may include an ejection button 201, a visual display 202, a housing 204, and a strip port connector 208, as shown in FIG. 1. Strip port connector 208 may be configured to receive test strip 100 when performing a test. Strip port connector 208 may also be referred to simply as a connector. Test strip 100 may include a sample receiving chamber 92, a distal end 3, and a sample inlet 90. A blood sample 94 can be applied to sample inlet 90 to fill sample receiving chamber 92, as illustrated in FIG. 1, so that an analyte measurement can be performed. Test meter 200 also includes suitable circuitry configured to determine whether a sample has filled sample-receiving chamber 92.

Figure 2:
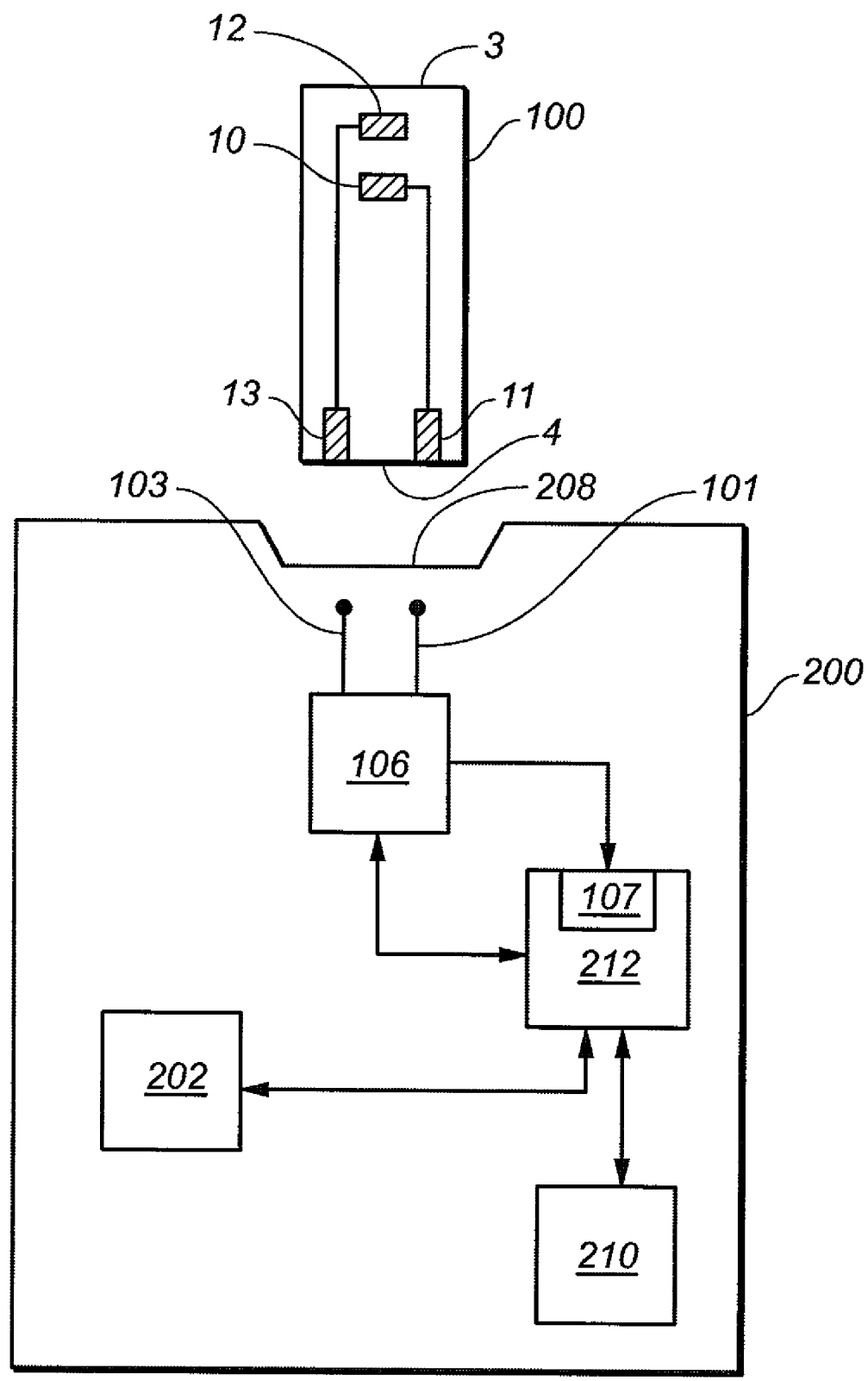
FIG. 2 is a functional block diagram of a test meter and a test strip.

FIG. 2 illustrates a functional block diagram of a test meter 200 and a test strip 100. Test meter 200 may include a strip port connector 208, a sensor interface circuitry 106, an A/D converter 107 (i.e., analog-to-digital converter), a processor 212, a memory unit 210, and a visual display 202. Processor 212 may include A/D converter 107 as an integrated functional unit. For example, a mixed signal microprocessor, such as the commercially available MSP 430 from Texas Instruments, may incorporate the functionality of an A/D converter.

Test strip 100 may include a working electrode 12, a reference electrode 10, a working contact pad 13, and a reference contact pad 11. Test strip 100 may further include a distal end 3 and a proximal end 4. Working contact pad 13 and reference contact pad 11 may be disposed at proximal end 4 and have an electrical connection to working electrode 12 and reference electrode 10, respectively. Working electrode 12 and reference electrode 10 may be disposed on distal end 3 and may also be disposed within sample receiving chamber 92.

Strip port connector 208 may be configured to receive a proximal end 4 of test strip 100 to form an electrical connection with working electrode 12 and reference electrode 10. Strip port connector 208 may include a working connector 103 and a reference connector 101, which are both configured to electrically connect to working contact pad 13 and reference contact pad 11. Working connector 103 and reference connector 101 may be made from an electrically conductive material suitable for carrying a current. In one embodiment, the conductive material may include a copper beryllium alloy plated with gold or a phosphor bronze plated with gold.

Sensor interface circuitry 106 may be configured to apply a test voltage (e.g., V) and also to measure a resulting test current (e.g., i(t) as a function of time t) between first working electrode 12 and reference electrode 10. When sensor interface circuitry 106 is applying a test voltage, it may be referred to as a potentiostat. Sensor interface circuitry 106 may be configured to measure a magnitude of the test current resulting from the application of the test voltage by converting the test current to a proportional voltage value (e.g., I/V converter) that is subsequently transferred to A/D converter 107.

Processor 212 may be configured to control and operate a measurement of a physiological fluid with test meter 200 and test strip 100. More specifically, processor 212 may be operatively linked so as to control the function of sensor interface circuitry 106, A/D converter 107, visual display 202, op-amp shut down circuit 600, and memory unit 210.

A/D converter 107 may be used to covert analog voltage values from sensor interface circuitry 106 to a digital value that is proportional to the measured test current. A/D converter 107 may communicate with sensor interface circuitry 106 and processor 212.

Memory unit 210 can be any suitable memory unit known to those of skill in the art including, for example, a solid-state nonvolatile memory units or an optical disk-based memory unit. In one embodiment, memory unit 210 may include both volatile and non-volatile memory portions. Memory unit 210 may be configured to contain software instructions to perform a glucose measurement using test meter 200 and test strip 100. Memory unit 210 may be configured to communicate with processor 212.

Visual display 202 can be, for example, any suitable display screen known to those of skill in the art including a liquid crystal display (LCD) screen. Suitable display screens include, without limitation, display screens that are configured to display tutorial images, including static graphics-based images (both with and/or without associated text) and animated graphics-based images (both with and/or without associated text). Visual display 202 may be used to illustrate a user interface for prompting a user on how operate test meter 200. Visual display 202 can also be used to perform other functions related to the operation of test meter 200 such as displaying a date, time and glucose concentration value as depicted in FIG. 1. An example of a tutorial for instructing a user on how to perform a measurement that is integrated into test meter 200 may be found in filed application No. 60/842,584 (filed on Sep. 5, 2006), which is hereby fully incorporated by reference herein.

In an exemplary embodiment, an electrochemical measurement of glucose may include an open circuit for a pre-determined time interval. During an open circuit, reduced mediator (e.g., ferrocyanide) may be generated through a reaction with a substrate (e.g., glucose) and an enzyme (e.g., glucose oxidase) in sample receiving chamber 92. After the reduced mediator is generated in a manner proportionate to the analyte concentration, a test voltage may be applied to perform the measurement. The following will describe embodiments of a sensor interface circuitry 106 that can apply an open circuit for a first pre-determined time interval and a test voltage for a second pre-determined time interval.

Figure 3:
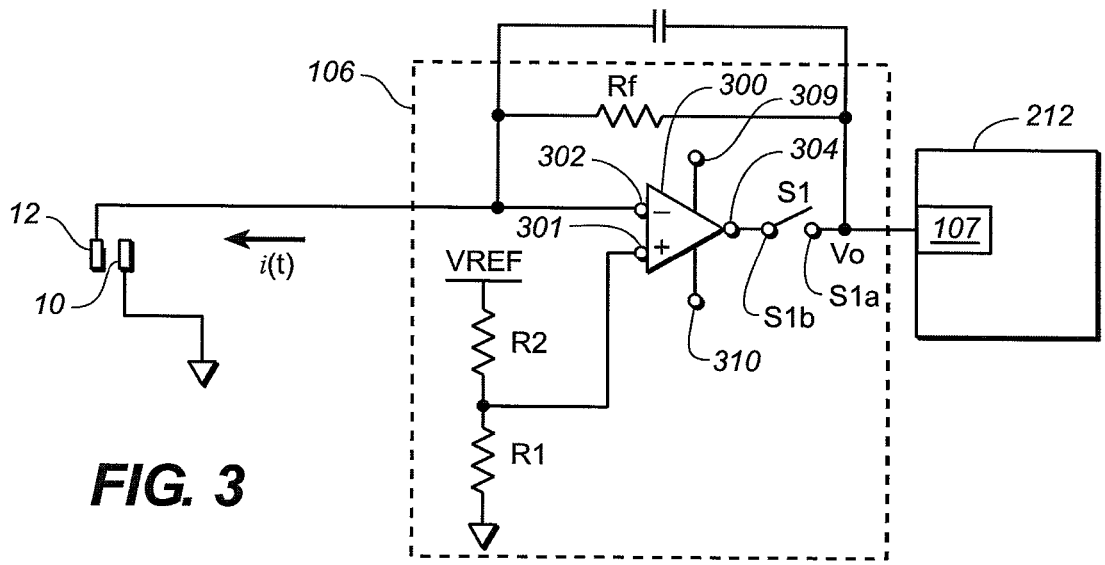
FIG. 3 illustrates a simplified diagram of a sensor interface circuitry where a first side of a switch is connected to an A/D converter and a feedback resistor, and a second side of the switch is connected to an output of an operational amplifier.

FIG. 3 illustrates an embodiment of a sensor interface circuitry 106 using a switch S1 that does not have a low resistance, but does not cause an uncompensated voltage drop. Sensor interface circuitry 106 includes an operational amplifier 300, a feedback resistor Rf, a first voltage divider resistor R1, a second voltage divider resistor R2, and a reference voltage source VREF. Operational amplifier 300 may include an output 304, an inverting input 302, a first power supply pin 309, a second power supply pin 310, and a non-inverting input 301. It should be noted that sensor interface circuitry 106 may also be referred to as a transimpedance amplifier, which includes an operational amplifier connected to other electronic components such as resistors and a reference voltage source. Optionally, a capacitor may be placed in parallel with the feedback resistor Rf for filtering out noise, as shown in FIG. 3.

Non-inverting input 301 may be connected to reference electrode 10 and reference voltage source VREF. A voltage divider that may use first voltage divider resistor R1 and second voltage divider resistor R2 for dividing the reference voltage source VREF into an output voltage of the reference voltage circuit. The combination of reference voltage source VREF and the voltage divider may also be referred to as a reference voltage circuit. Reference electrode 10 may be connected to a ground through a second line, as shown in FIG. 3.

A feedback resistor Rf may be connected to an inverting input 302 and to a first side S1a of switch S1, as shown in FIG. 3. The first side S1a may also be connected to A/D converter 107, as shown in FIG. 3. A second side S1b of switch S1 may be connected to output 304, as shown in FIG. 3. Switch S1 may be operatively connected to processor 212 to control when to initiate an opening or closing process. Thus, when switch S1 is closed, the test current pathway along a first line does not pass through switch S1 effectively preventing an uncompensated voltage drop. The first line may be a current pathway that flows from working electrode 12 to A/D converter 107 via feedback resistor Rf. In the absence of an uncompensated resistance, the test voltage applied along the first line may be substantially equivalent to the output voltage. The output voltage Vo of the transimpedance amplifier is taken from the connection between feedback resistor Rf and first side S1a of switch S1 to prevent any inaccuracy in the test current measurement because of the switch resistance. It should also be noted that the resistance of switch S1 would not impact the accuracy of the test current measurements using a current to voltage functionality of the transimpedance amplifier so long as the resistance is sufficiently small to prevent saturation.

Switch S1 may have a finite resistance Rs that could potentially cause an uncompensated voltage drop to occur between working electrode 12 and reference electrode 10. For example, if switch S1 were placed along the first line, then the effective applied test voltage would be Veff=V−i(t)Rs. The term i(t)Rs represents an uncompensated voltage drop. When Veff becomes sufficiently low (e.g., <<redox voltage of the mediator) because of a relatively high resistance Rs or a relatively high current i(t) or a combination thereof, the resulting test current may give an inaccurate glucose concentration.

Figure 4:
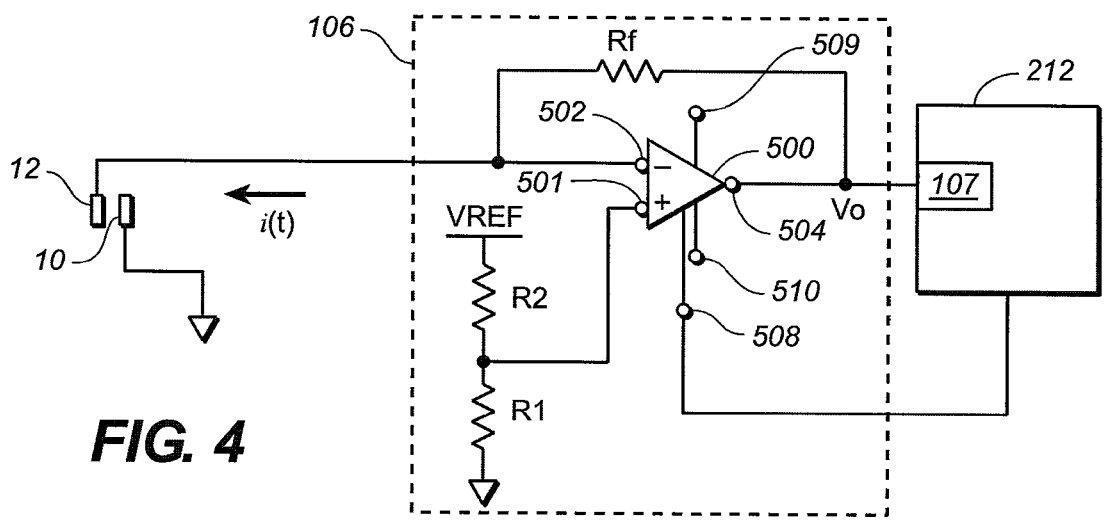
FIG. 4 illustrates a simplified diagram of a sensor interface circuitry using an operational amplifier having a shut down control circuit.

FIG. 4 illustrates another embodiment of a sensor interface circuitry 106 that can create an open circuit without causing an uncompensated voltage drop. Instead of using a switch S1, sensor interface circuitry 106 can create an open circuit using an operational amplifier 500 having a shutdown pin 508 in conjunction with a shutdown control circuit built into the operational amplifier, of which an example of a similar control circuit is shown here in FIG. 5 as shutdown circuit 600. Similar to operational amplifier 300, operational amplifier 500 may include an inverting input 502, a non-inverting input 501, a first power supply pin 509, a second power supply pin 510, and an output 504. The shutdown circuit 600 may be activated (e.g., by connecting shut down pin 508 to a logical low of the processor 212) to turn off operational amplifier 500 so as to create an open circuit between working electrode 12 and reference electrode 10. Additionally, shutdown circuit 600 may be de-activated (e.g., via connection of shut down pin 508 to logical high of processor 212) to turn on operational amplifier 500 to apply a test voltage between working electrode 12 and reference electrode 10. An example of such operational amplifier is available from Texas Instrument as a Wideband, Ultra-Low Noise, Voltage Feedback Operational Amplifier with Shutdown Model OPA847. The use of shutdown circuit (such as the one shown in FIG. 5) in an operational amplifier allows an open circuit to be created in an analyte measurement circuit (or system) without a switch, such as switch S1 that is shown in FIG. 3, and which open circuit does not cause an uncompensated voltage drop to occur when a test voltage is applied.

Figure 5:
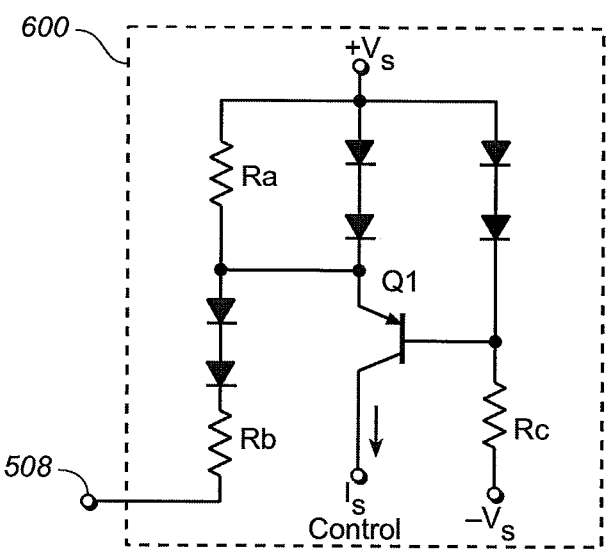
FIG. 5 illustrates a simplified shut down control circuit for an operational amplifier such as one utilized in FIG. 4.

Referring to FIG. 5, if shut down pin 508 is left unconnected, the op-amp operates without any shut down function. Upon pin 508 being connected to logical low, base current to Q1 is provided to the Rc resistor. As shut down pin 508 is pulled low (via processor 212), additional current is pulled through resistor Ra so as to turn on the diodes. Any further current pulled through shut down pin 508 results in the emitter base voltage of Q1 at approximately 0V, which shuts of the collector current out of Q1 and turning the amplifier off in typically about 200 nanoseconds. Depending on external resistors, the shut down time may be longer than 200 nanoseconds due to longer nodes discharge.

Applicants believe that they have discovered certain problems that were not recognized in the art in the utilization of a switch interposed at any point in current conductive path between the electrode and the transimpedance amplifier in the known device. For instance, a galvanic potential can develop between a working electrode and reference electrode that is outside the limits of the supply voltage when the test meter applies an open circuit, which can cause the open circuit to be corrupted. Such a corruption can occur because the protection diodes inside the operational amplifier chip do not have a true high impedance node when in the shut down mode. A corrupted sensor interface circuitry 106 may apply a nominal voltage or current instead of an open circuit. In order for operational amplifier (300 or 500) to function properly, an appropriate supply voltage should be applied to first power supply pin (309, 509) (e.g., +3 Volts) and second power supply pin (310, 510) (e.g., ground or zero Volts). A power supply voltage having a limit of zero volts and +3 Volts may be selected for convenience because it can be created using a combination of two disposable alkaline batteries (e.g., two AA batteries) or a lithium battery without additional circuitries.

For a typical glucose test strip, a galvanic potential with respect to the reference electrode can possibly develop on the test strip that is outside of the supply voltage limits (+3 Volts and zero Volts) during an open circuit time interval causing the protection diode to prevent the application of a true open circuit. However, it may be unlikely that the galvanic potential may become greater than +3 Volts or less than zero Volts for a typical glucose test strip using an inert conductive electrode and a ferricyanide mediator. A galvanic potential may be a voltage that arises from a differential concentration of a chemical species and/or the type of chemical species present with respect to the working electrode and the reference electrode, which can be estimated using the Nernst equation. An example of a device commonly known to generate a galvanic potential may be a battery.

In an embodiment, sensor interface circuitry 106 may be configured to provide an open circuit that is robust to the development of a negative galvanic potential by using a supply voltage having a limit of −3 Volts and +3 Volts to expand the open circuit operating range for the possible potentials that may develop across the strip. It should be noted that a supply voltage having a limit of −3 Volts and +3 Volts may be more inconvenient to implement than having the limit of zero volts and +3 Volts because of the need for using 4 alkaline batteries or for more expensive electronic components.

Applicants have also discovered that in certain instances, that selection of just any the operational amplifier with a shut down circuit for use in an analyte circuit may not be suitable for its intended use in a test meter as such op-amp may be required to meet at least one operational parameter that is believed to be previously unrecognized. Specifically, various operational amplifiers with a shut down control circuit were found by the applicants to have a leakage current when the shut down control circuit is activated. Such leakage current can cause a nominal voltage or current to be applied between working electrode and reference electrode when the test meter is attempting to apply an open circuit. If the leakage current is sufficiently large during an open circuit, then an inaccurate analyte concentration may result. Thus, in order to apply an open circuit that is not substantially contaminated by a leakage current, an operational amplifier with a shut down control circuit may be required to have a low leakage current. Although the leakage current is not a typical design specification of operational amplifiers having a shut down control circuit, applicants found that operational amplifiers OPA2334 and TLV2763 from Texas Instruments (Dallas, Tex.) were suitable for use as an embodiment. An operational amplifier 500 may be selected that has a leakage current of less than about one nanoampere when the shutdown circuit 600 is activated for use in an electrochemical glucose test meter.

A shut down control circuit of an operational amplifier was also found to have a relatively slow response time for being activated and deactivated compared to solid-state switches. The typical response time of a shut down control circuit requires on the order of a microsecond compared to a solid-state switch that requires on the order of a nanosecond. Thus, a shut down control circuit may be about 1000 times slower than the response time of a solid-state switch. However, applicants have found that the slow response time of the shut down control circuit does not influence the accuracy of a typical glucose test strip measurement when using the shut down control circuit for creating an open circuit.

In a method embodiment of electrochemically testing test strip 100, test meter 200 may detect a presence of a physiological sample disposed on working electrode 12 and reference electrode 10. Examples for detecting the presence of a physiological sample may be found in U.S. Pat. Nos. 6,193,873; 5,266,179; and 5,366,609, which are hereby fully incorporated by reference herein. After detecting the presence of the physiological sample, switch S1 may be in the open state to provide an open circuit for a first pre-determined time interval between working electrode 12 and reference electrode 10. During the test, operational amplifier 300 may be powered by a supply voltage having a limit of zero Volts and +3 Volts. Next, switch S1 may be closed so that a test voltage may be applied for a second predetermined time interval between working electrode 12 and reference electrode 10. A magnitude of a resulting test current value may be measured during the second predetermined time interval and the resulting test current value may be correlated to an analyte concentration value.

In another method embodiment of electrochemically testing test strip 100, test meter 200 may detect a presence of a physiological sample disposed on working electrode 12 and reference electrode 10. After detecting the presence of the physiological sample, shutdown circuit 600 may be activated to turn off operational amplifier 500 to provide an open circuit for a first pre-determined time interval between working electrode 12 and reference electrode 10. During the test, operational amplifier 500 may be powered by a supply voltage having a limit of zero Volts and +3 Volts. Next, shutdown circuit 600 may be de-activated to turn on operational amplifier 500 so that a test voltage may be applied for a second predetermined time interval between working electrode 12 and reference electrode 10. A magnitude of a resulting test current value may be measured during the second predetermined time interval and the resulting test current value may be correlated to an analyte concentration value.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods within the scope of these claims and their equivalents be covered thereby.

What is claimed is:

1. In a system to determine analyte concentration in a sample, the system comprising:
    a test meter which receives a test strip and detects and displays a concentration of an analyte in the sample through electrochemical or electrical testing, the improvement comprising:
    a test strip connector having a first line configured to connect to a first electrode of a test strip and a second line configured to connect to a second electrode of the test strip;
    a reference voltage circuit that provides an output voltage;
    an operational amplifier connected to the reference voltage circuit to provide a test voltage to the first line that is substantially equal to the output voltage, the operational amplifier having an output configured for one of a connected or disconnected state to the first line; and
    a processing circuit connected to the output of the operational amplifier and the first line such that, during a disconnected state between the output and the first line, the processing circuit remains in connection with the first line.

2. The system of claim 1, further comprising a switch disposed between the output and the
    first line so that a nominal resistance of the switch in a closed state does not cause an uncompensated voltage drop between the working electrode and the reference electrode when the connector is coupled to the working electrode and the reference electrode.

3. The system of claim 1, in which the operational amplifier comprises a shut down logic circuit connected to the processing circuit.

4. A circuit for analyte measurement, the circuit comprising:
    a test strip connector having a first line configured to connect to a first electrode of a test
    strip and a second line configured to connect a second electrode of the test strip to a ground;
    an operational amplifier having a first input connected to a reference voltage circuit and a second input connected to both the first line and to an output of the operational amplifier via a feedback resistor; and
    a switch disposed between the output and the second input of the operational amplifier to connect the output to the first line in a closed state of the switch and to disconnect the output from the first line in an opened state of the switch.

5. The circuit of claim 4, in which the reference voltage circuit comprises a reference
    voltage source and a voltage divider.

6. The circuit of claim 5, in which the output of the operational amp and the first line are connected to a filter.

7. The circuit of claim 6, in which the filter comprises a capacitor.

8. A circuit for analyte measurement, the circuit comprising:
    a test strip connector having a first line configured to connect to a first electrode of a test strip and a second line configured to connect a second electrode of the test strip to a ground;

a reference voltage circuit that provides an output voltage;

an operational amplifier having a first input connected to a reference voltage circuit and a second input connected to both the first line and to an output of the operational amplifier via a feedback resistor, the operational amplifier further including a shut down circuit configured to place the operational amplifier in a shut down mode a processing circuit connected to the output of the operational amplifier and the first line such that, during a disconnected state between the output and the first line, the processing circuit remains in connection with the first line.

9. The circuit of claim 8, in which the operational amplifier comprises an operational amplifier with leakage current of less than about one nanoampere upon activation of the shut down circuit.

10. The circuit of claim 8, in which the reference voltage circuit comprises a reference voltage source and a voltage divider.

11. The circuit of claim 10, in which the output of the operational amp and the first line are connected to a filter.

12. The circuit of claim 11, in which the filter comprises a capacitor.

* * * * *